United States Patent [19]

Bartels

[11] 4,311,317
[45] Jan. 19, 1982

[54] LIP AND RADIAL SEAL

[76] Inventor: Harold U. Bartels, 2729 Harrison, Riverside, Calif. 92503

[21] Appl. No.: 68,245

[22] Filed: Aug. 20, 1979

[51] Int. Cl.$^3$ .............................................. F16J 15/10
[52] U.S. Cl. ........................... 277/212 C; 277/207 A; 277/DIG. 2
[58] Field of Search .......... 277/212 C, 212 F, 212 L, 277/207 A, DIG. 2

[56] References Cited

U.S. PATENT DOCUMENTS 2,668,067  2/1954  Fitzsimmons .................... 277/212 F
3,046,028  7/1962  Nathan ............................. 277/212 C Primary Examiner—Robert I. Smith

[57] ABSTRACT

An annular ring having a sealing lip and having two or more annular beads, is installed in a groove. Interacting dimensions of ring and groove are such that the height of one bead added to the thickness of the ring is less than the width of the groove while the height of two opposed beads together plus the thickness of the ring is greater than the width of the groove. The annular beads are formed on the ring such that the ring must deform in order to fit into the groove. Deformation of the ring is accompanied by an angular displacement of the sealing lip so as to form a positive seal.

15 Claims, 11 Drawing Figures

LIP AND RADIAL SEAL

BACKGROUND OF THE INVENTION

1. Field of the Invention

This invention relates generally to humidifiers as used in medical respiratory apparatus, and more particularly to means for sealing these devices.

2. Description of the Prior Art

Humidifiers are known in which adequate seals are effected between the jar assembly and the cover, however, removal for cleaning and reinstallation after accomplishment of cleaning have presented difficulties. In some instances, it has been impossible to refit the sealing gasket into its retaining groove and in other instances, a good seal could not be formed. All prior art devices examined or known have depended on the displacement of squeezed rubber for effecting a seal. Such displacement has caused permanent deformations and even cracks in the material of the sealing gasket thus resulting eventually in permanent leaks.

A novelty search conducted in the United States Patent and Trademark Office to locate patents relevant to the above topic did not disclose any patents contemplating a combination of a lip seal/radial seal for medical humidifiers. Two patents showing the general concept of a lip seal with beads, however, were discovered. The following are, therefore, considered to be of potential interest:

| U.S. Pat. No. | Title | Inventor |
| --- | --- | --- |
| 2,329,028 | "Oil Seal" | H. M. Austin |
| 3,112,114 | "Sealing Gasket for Beverage Dispenser" | W. H. Jacobs |

The fields of search were:

| Class | 215 | Subclass | 345 |
| --- | --- | --- | --- |
| | 277 | | 212F |
| | | | 152 |
| | | | 165 |

It would thus be a great advantage to the art to provide a means to form a good seal without causing permanent deformation of the material of the sealing member.

Another great advantage would be the provision of a sealing member that is easy to remove for cleaning.

A further desirable advantage would be the provision of a sealing member that is easy to reinstall.

Yet another advantage would be the provision of the above advantages in an uncomplicated and economical structure.

SUMMARY OF THE INVENTION

In light of the advantages sought to be accomplished in the instant invention, it is thus an object of the present invention to provide a means to form a good seal without causing permanent deformation of the material of the sealing member.

Another object of the instant invention is to provide a sealing member that is easy to remove for cleaning.

A further desirable object of the instant invention is to provide a sealing member that is easy to reinstall after removal.

Still another object of the present invention is to provide a sealing structure meeting the above stated objects in an economical and uncomplicated fabrication.

In the accomplishment of these and other objects, a lip radial seal is provided in which the axially sealing lip is substantially unaltered from prior art, however, the radial seal and installation parameters are substantially improved by discrete modifications in the form of annular rings. In the device of the invention, the basic sealing structure is made of a lesser dimension than the mating groove so as to facilitate installation. This sealing structure, however, incorporates annular beads such that sealing and mechanical retention are effected by the beads as will be shown.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
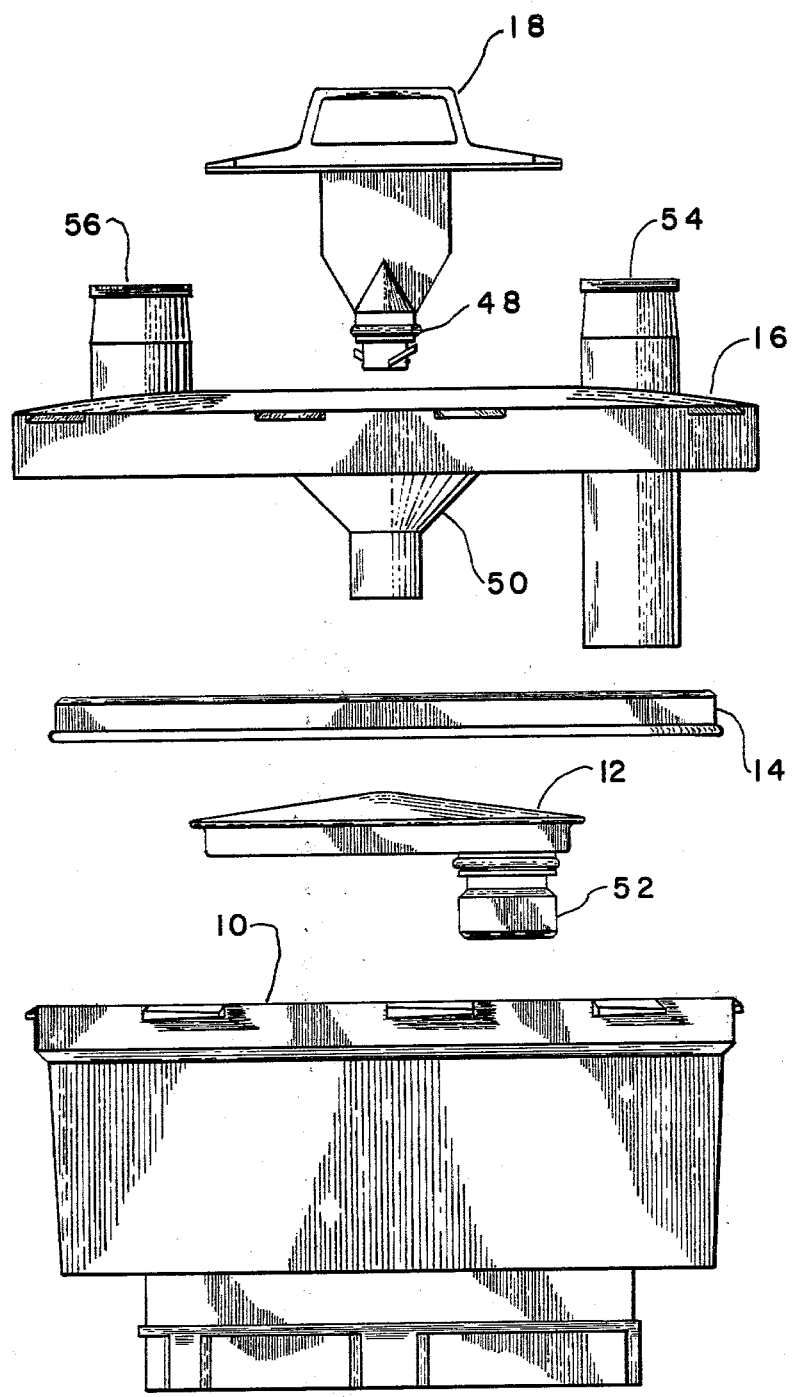
FIG. 1 is an idealized conceptualized drawing showing the principal elements of a humidifier system.

Referring to FIG. 1 with greater particularity, a system in which the present invention might be utilized is illustrated. The basic jar assembly 10 accepts a heater assembly 12 having a connector assembly 52. A lip seal 14 effects the sealing of chamber cover 16 to the basic jar assembly 10. It is this lip seal to which the major attention is to be directed. The chamber cover 16 is entirely conventional, having a breathing gas inlet 54 and an outlet 56. Liquid may be added to the system by means of the unconventional funnel 50 which may then be sealed off by the application of filler cap 18 having an O-ring 48.

Figure 2:
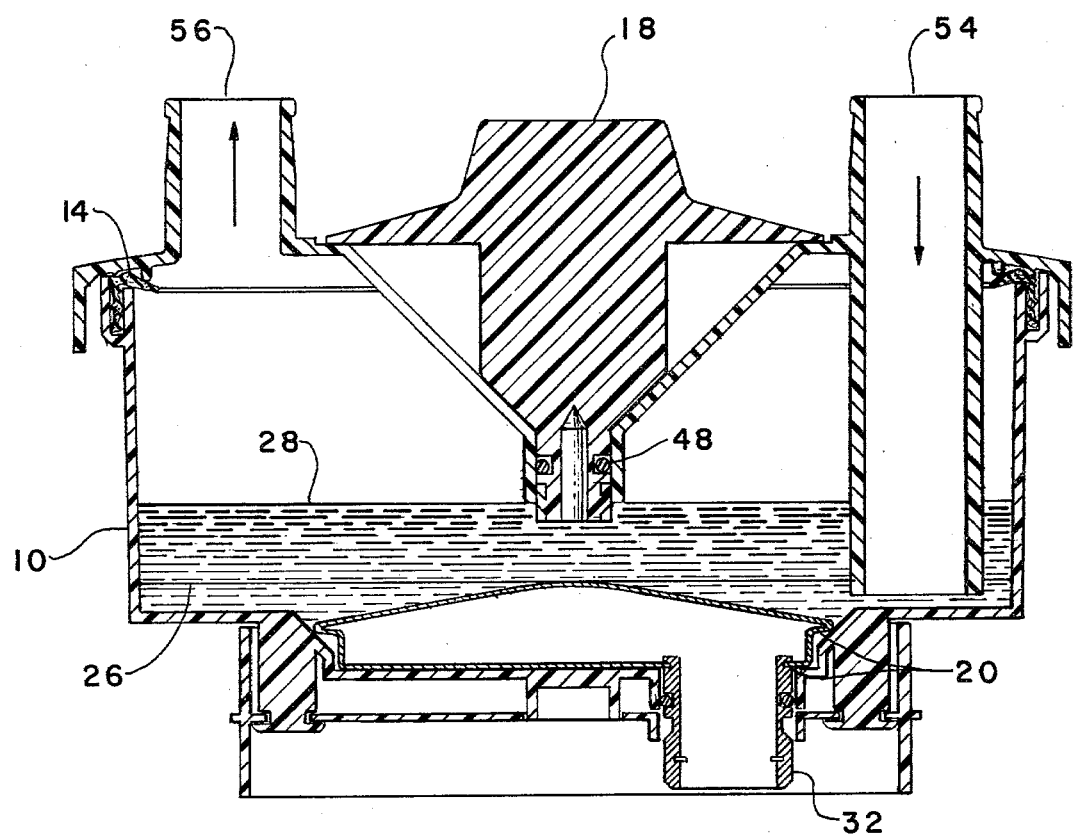
FIG. 2 is a cross-section of the assembled humidifier system.

FIG. 2 shows the assembled unit in cross-section and further illustrates the high and low fluid level marks 28 and 26 respectively. O-ring 48 is shown as it fits into the funnel and the lip seal 14 is shown as pressed down by the cover. The shroud 32 is pointed out for the connector assembly and the heater hermetic seals 20 are pointed out.

Figure 3:
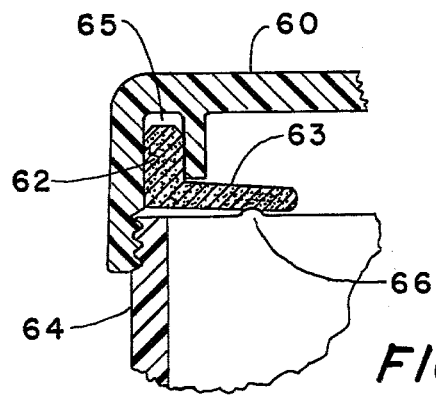
FIG. 3 is a cross-section of a prior art gasket fitted into a groove.
Figure 4:
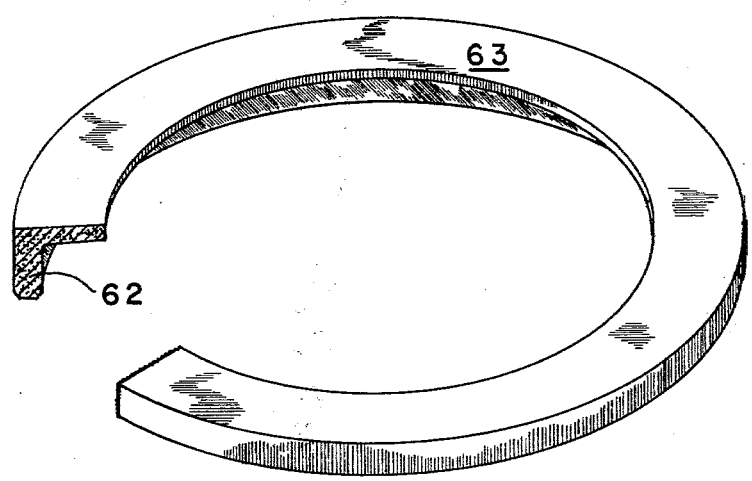
FIG. 4 is a perspective drawing of a prior art gasket cut so as to further illustrate a prior art sealing member.
Figure 4A:
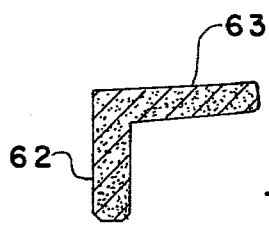
FIG. 4a is a profile of a cross-section of a prior art sealing gasket.

Referring now to FIGS. 3, 4, and 4a, some examples of prior art sealing means may be explained. Examination of FIG. 3 will show that a positive seal depends, among other things, on an interference fit between the prior art lip seal gasket's thick shank 62 and the prior art cover channel 65. That is to say, the fit between the gasket and the groove must be tight enough to prevent the escape of steam and other fluids. As shown, the prior art cover 60 screws onto the prior art jar 64 forcing the gasket downward and also forcing the prior art lip seal gasket's thin shank 63 against a prior art positive seal promontory 66. FIG. 4 is an idealized perspective of a partially cutaway lip seal gasket, offered to clarify and further illustrate the circular nature of the sealing gasket. In FIG. 4a, the conventional, greater-than-90 degree angle between prior art lip seal gasket's thin shank 63 and prior art lip seal gasket's thick shank 62 may be noted. The purpose of this greater-than-90 degree configuration is to effect a more positive seal when thin shank 63 contacts promontory 66 as shown in FIG. 3. It should be noted at this point that prior to the present invention, the forcing down of cover 60 by screwing it onto jar 64 could be expected to cause some displacement of thick shank 62 along the channel 65. This displacement would, of course, be unpredictable and its subsequent relaxation would also be unpredictable thus even when a positive seal had been effected, its integrity and duration were questionable.

Figure 5:
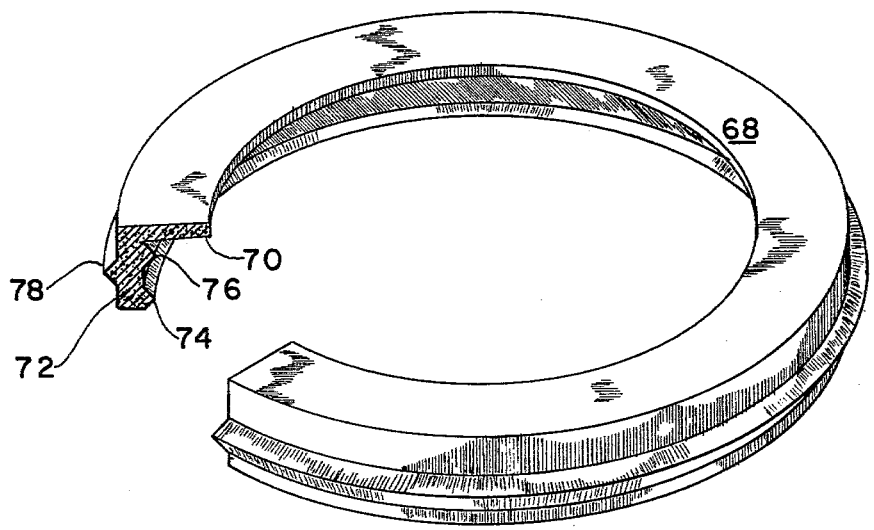
FIG. 5 is a perspective drawing, partly in cross-section, of the sealing member of the invention.
Figure 5A:
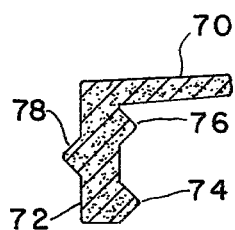
FIG. 5a is a profile of a cross-section of the sealing member of FIG. 5.

Referring now to FIGS. 5 and 5a, the lip sealing gasket 68 contemplated by the invention is shown in one embodiment. The device comprises a sealing gasket thick shank 72 having first, second and third sealing beads 74, 76 and opposed bead 78 respectively. Sealing gasket thin shank 70 is angularly removed from thick shank 72 by, preferably, slightly more than 90 degrees as is conventional and as may be more readily seen by referring to FIG. 5a. The dimensions involved are such that the annular ring 68 has a thick shank 72 of a thickness much less than the annular slot into which it is to fit.

Figure 6:
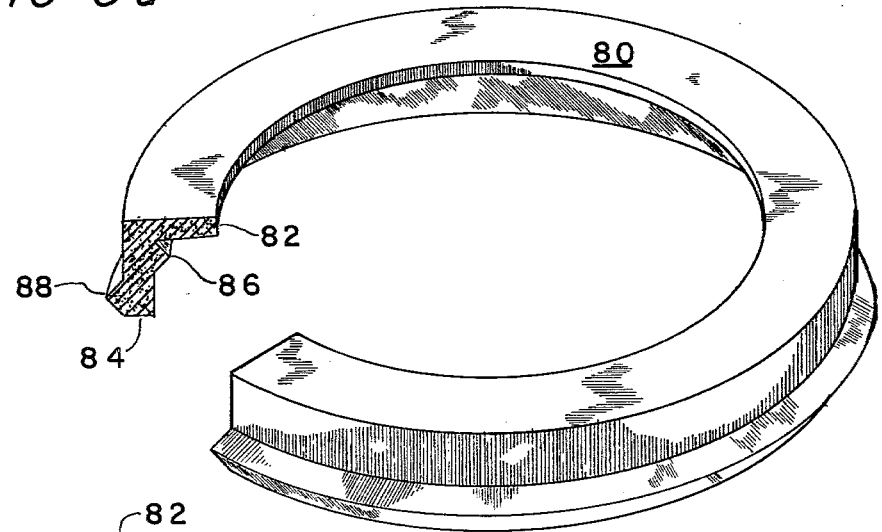
FIG. 6 is a perspective drawing, partly in cross-section, of the sealing member of another embodiment of the sealing member as contemplated by the invention.
Figure 6A:
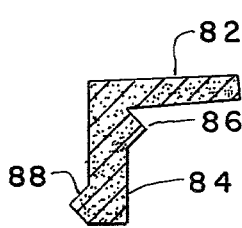
FIG. 6a is a profile of a cross-section of the sealing member of FIG. 6.

FIGS. 6 and 6a illustrate another embodiment in which the sealing gasket 80 comprises a sealing gasket thick shank 84, a sealing gasket thin shank 82 and first and second sealing beads 86 and opposed bead 88. Thus this embodiment contemplates only two sealing beads instead of three. Either configuration, that considered in FIGS. 5 and 5a or that considered in FIGS. 6 and 6a, has been found to work well in practice.

Figure 7:
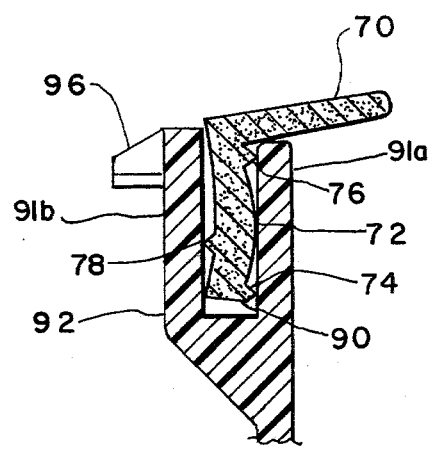
FIG. 7 is an enlarged detail of a cross-sectional elevation showing the sealing gasket installed in its mating groove.
Figure 7A:
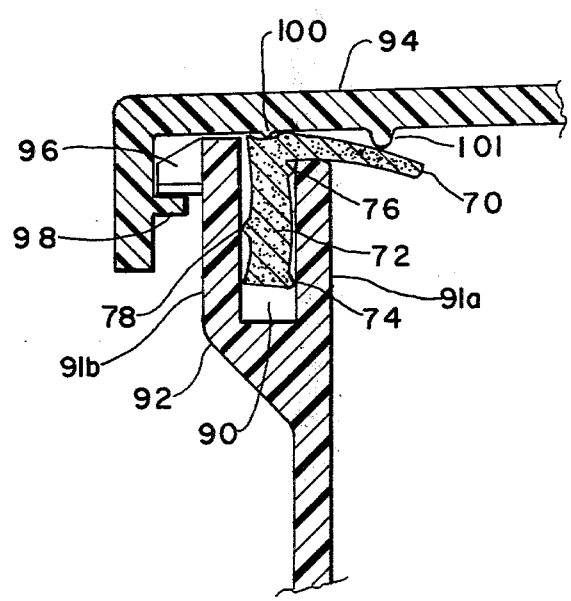
FIG. 7a is an enlarged detail of a cross-sectional elevation showing the positive seal effected when the cover is installed.

Reference now to FIGS. 7 and 7a allows a more thorough explanation of the operation of the sealing gasket as contemplated by the invention. The sealing gasket is fit into a sealing gasket channel or annular slot 90 and is of such dimensions that the sealing gasket thick shank 72 is smaller than the width of the annular slot 90. The axial depth of the gasket, however, is such that all the sealing beads 74, 76 and opposed bead 78 contact the sides of the annular slot 90. The channel 90, of course, is formed into the vessel to be sealed 92. The slot 90 is formed between an inner rim member 91a and an outer rim member 91b. The relative dimensions between sealing gasket 68 and channel 90 are such that sealing gasket thin shank 70 is forced into an even greater angular separation from sealing gasket thick shank 72 than the normal more than 90 degree angular separation. With respect to the annular sealing beads, the dimensions are such that the dimensions of each bead alone added to the thickness of the thick shank 72 is less than the width of the annular slot 90, however, the dimensions of the opposed beads 76 plus 78 and/or 74 plus 78 added to the thick shank 72 are greater than the width of the annular slot 90. The inner rim member 91a of the slot forces added angular displacement of sealing gasket thin shank 70 with additional forcing of the gasket thick shank 72 into annular slot 90.

It may be seen by reference to FIG. 7a that the sealing beads are so placed on the thick shank 72 that the shank must bow in order to be installed in annular slot 90. This forced bending of the shank 72 provides a more even and predictable sealing force on the beads than the more usual squeezing of the thick shank and thus the occurrence of a permanent set of the material of the gasket is minimized. When sealing cover 94 is attached to the vessel to be sealed 92 by means of cover retaining lip 96 and cover retainer 98, thick shank 72 assumes a bowed configuration in response to forces impressed by the interaction of the sealing beads 74, 76 and 78 with the sides of the annular slot 90. Thin shank 70, after having been forced upward by the inner member of the annular slot 90, is now forced down by second positive annular sealing promontory 101. First positive annular sealing promontory 100 acts to maintain the insertion of the thick shank 72 into annular slot 90.

Thus there has been described a lip radial seal that will effect a reliable positive seal on a humidifier system while at the same time providing for ease of disassembly and reassembly. Great improvements in integrity of seal, reliability of reassembly, flexibility, maintainability, ease of operation and safety have been provided through the novel advantages of the invention.

It is pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. A fluid-tight sealing assembly for a vessel having a removable cover, comprising:

inner and outer rim members around the open end of said vessel, forming a slot therebetween;

a resilient sealing gasket having first and second shanks joined at approximately a right angle;

interior and exterior bead means formed on opposite sides of said first shank, said interior and exterior bead means being nonaligned with each other along the axial dimension of said first shank;

said first shank, said slot, and said interior and exterior bead means being dimensioned such that the thickness of said first shank plus one of said bead means is less than the width of said slot, and the thickness of said first shank plus two of said bead means on opposite sides of said first shank is greater than the width of said slot, whereby the insertion of said first shank into said slot results in a bowing of said first shank along the axial dimension thereof; and sealing means for forming a positive seal with said second shank and said inner rim member when said cover is attached to said vessel.

2. The fluid tight sealing assembly of claim 1, wherein said interior bead means comprises at least one peripheral bead formed interiorly on said first shank, and said exterior bead means comprises at least one peripheral bead formed exteriorly on said first shank.

3. The fluid-tight sealing assembly of claim 1, wherein said first shank is thicker than said second shank.

4. The fluid-tight sealing assembly of claim 1, wherein said first and second shanks are joined at an angle of slightly more than 90 degrees.

5. The fluid-tight sealing assembly of claim 1, wherein said sealing means comprises a promontory formed on the interior of said cover.

6. The fluid-tight sealing assembly of claim 5, wherein said slot, said gasket, and said first promontory are substantially annular.

7. A fluid-tight sealing assembly for a vessel having a removable cover, comprising:
inner and outer rim members around the open end of said vessel, forming a slot therebetween;
a resilient gasket having first and second shanks joined at approximately a right angle, said first shank having a thickness which is less than the width of said slot;
bead means on said first shank for causing said first shank to bow along its axial dimension when said first shank is inserted into said slot;
sealing means for forming a positive seal with said second shank and said inner rim member when said cover is attached to said vessel; and
attachment means for removably attaching said cover to said vessel such that said sealing means is maintained in forceful engagement against said second shank, thereby maintaining said positive seal.

8. The fluid-tight sealing assembly of claim 7, wherein said bead means comprises:
at least one substantially continuous interior bead formed on the interior of said first shank so as to underlay said second shank, and at least one substantially continuous exterior bead formed on the exterior of said first shank;
said interior and exterior beads being located along the axial dimension of said first shank such that the maximum width of said first shank, at any point along is axial dimension, equals the thickness of said first shank plus the thickness of one of said beads, said maximum thickness being slightly less than the width of said slot.

9. The fluid-tight sealing assembly of claim 7, wherein said sealing means comprises a promontory formed on the interior of said cover.

10. The fluid-tight sealing assembly of claim 9, wherein said slot, said gasket, and said promontory are substantially annular.

11. The fluid-tight sealing assembly of claim 10, wherein said promontory is a first promontory, and further comprising:
a second substantially annular promontory formed on the interior of said cover radially outwardly from said first promontory, and located with respect to said gasket, when said cover is attached to said vessel, so as to maintain said first shank in said slot.

12. The fluid-tight sealing assembly of claim 7, wherein said attachment means comprises:
a retaining lip on the exterior of said outer rim member; and
retention means on said cover for engaging said retaining lip.

13. A fluid-tight sealing assembly for a vessel having a removable cover comprising:
inner and outer rim members around the open end of said vessel, forming a slot therebetween;
a resilient gasket having first and second shanks joined at approximately a right angle, said first shank having a thickness which is less than the width of said slot;
at least one interior bead formed interiorly on said first shank;
at least one exterior bead formed exteriorly on said first shank;
said interior and exterior beads being located along the axial dimension of said first shank such that the maximum width of said first shank, at any point along the axial dimension thereof, equals the thickness of said first shank plus one of said beads, said maximum thickness being slightly less than the width of said slot, the thickness of said first shank plus the thicknesses of one interior bead and one exterior bead being slightly greater than the width of said slot, so that the insertion of said first shank into said slot results in a bowing of said first shank along the axial dimension thereof;
said insertion also causing an engagement between said inner rim member and said second shank, said engagement increasing the angular displacement between said first and second shanks;
first and second promontories formed on the interior of said cover, said first promontory being engageable against said second shank to push said second shank toward said inner rim member, and said second promontory being engageable with said gasket approximately at the juncture between said first and second shanks to maintain the insertion of said first shank into said slot; and
means for removably attaching said cover member to said vessel such that said first promontory is maintained in forceful engagement against said gasket, thereby forming a fluid-tight seal by the engagement between said inner rim member, said second shank, and said first promontory.

14. The fluid-tight sealing assembly of claim 13, wherein said slot, said gasket, and said first and second promontories are substantially annular, said second shank extends radially inwardly from said first shank, and said second promontory is located radially outwardly from said first promontory.

15. The fluid-tight sealing assembly of claim 13, wherein said means for removably attaching said cover comprises:
a retaining lip on the exterior of said outer rim member; and
retention means on said cover for engaging said retaining lip.